United States Patent [19]

Van Kruchten et al.

[11] Patent Number: 5,089,158
[45] Date of Patent: Feb. 18, 1992

[54] ADDITIVES FOR LUBRICATING OILS AND PROCESSES FOR PRODUCING THEM

[75] Inventors: Eugene M. G. A. Van Kruchten; Gerardus W. J. Heimerikx, both of Amsterdam, Netherlands

[73] Assignee: Shell Oil Company, Houston, Tex.

[21] Appl. No.: 577,985

[22] Filed: Sep. 5, 1990

[30] Foreign Application Priority Data

Sep. 5, 1989 [GB] United Kingdom ............... 8920041

[51] Int. Cl.$^5$ .................... C07C 63/00; C10M 129/59
[52] U.S. Cl. .................................. 252/51.5 A; 252/25; 564/177

[56] References Cited

U.S. PATENT DOCUMENTS

| | | | |
|---|---|---|---|
| 2,848,418 | 8/1958 | Miller et al. | 252/51.5 |
| 2,959,550 | 11/1960 | Young et al. | 252/40.7 |
| 4,090,971 | 5/1978 | Hoke | 252/51.5 A |
| 4,795,832 | 1/1989 | Leinen | 564/177 |

FOREIGN PATENT DOCUMENTS

| | | |
|---|---|---|
| 0267658 | 9/1987 | European Pat. Off. |
| 594954 | 6/1959 | Italy ................. 564/177 |
| 698971 | 10/1953 | United Kingdom . |
| 786167 | 11/1957 | United Kingdom . |
| 853295 | 3/1961 | United Kingdom . |

Primary Examiner—Brian E. Hearn
Assistant Examiner—Maria Nuzzolillo

[57] ABSTRACT

The invention provides oil-soluble multivalent metal ion salts of a compound of the formula $XNR^1R^2$, in which $R^1$ and $R^2$ are the same or different and each are selected from hydrogen and hydrocarbon based radicals having from 1 to 30 carbon atoms, X is an acyl radical of an aromatic ortho-hydroxy carbozxyic acid having a ring substituent which is a hydrocarbon based radical having at least 4 carbon atoms, a process for their preparation, and their use, as additives, in lubricating oils.

2 Claims, No Drawings

ADDITIVES FOR LUBRICATING OILS AND PROCESSES FOR PRODUCING THEM

FIELD OF THE INVENTION

The present invention relates to a derivative of the amide of an aromatic carboxylic acid having an ortho-hydroxy group in the form of a salt with a multivalent metal ion, processes for producing such a salt and compositions containing it, especially lubricating oil compositions.

BACKGROUND OF THE INVENTION

The use of alkaline earth metal salts or organic carboxylic acids as additives for lubricating oil compositions is known. The said salts have a dispersant property so that they, when applied in such composition, ensure that the inside of engine cylinders remains clean and that deposition of carbonaceous products on pistons and in piston grooves is counteracted, so that piston-ring sticking is prevented.

It is also known to prepare basic (or overbased) alkaline earth metal salts of such acids. The overbasing provides an alkaline reserve which, when applied in lubricating oil compositions, reacts with and neutralises acidic compounds formed during the operation of the engine in which the composition is applied. Hence, sludge which may arise, it maintained dispersed due to the dispersant property of the salt while acids which would enhance sludge formation are neutralized. It is often desired for such basic salts to have a basicity index (BI), defined as the equivalents ratio of the total of alkaline earth metal to the total of organic acid, which is as high as possible. Examples of the salts are described in Great Britain Patent No. A-786167.

Another class of detergent additives are the so-called ashless dispersants. In U.S. Pat. No. 4,090,971 amides alkyl-substituted salicylic acids are described. The amines used to make the amides may be monoamines, including hydroxyamines, but are preferably polyamines, including diamines, for instance alkylene polyamines.

In U.S. Pat. No. 2,848,418 amides of salicylic acids are described, particularly formed from primary amines whose nitrogen atom is linked to secondary or tertiary carbon atom, i.e. comprising a branched alkyl group. The amide is said to improve the stability of lubricating oils.

In U.S. Pat. No. 3,110,670 lubricating oils containing the barium salts of primary N-alkyl amides of salicylic and other benzene hydroxy carboxylic acids are claimed to give improvements in oxidation stability of lubricating oils. The benzene ring may have methyl, hydrogen, sulpho or amino substituents. The compounds are oxidation inhibitors.

In U.S. Pat. No. 2,959,550 N-alkyl amides of aromatic para-hydroxy carboxylic acids are described as oxidation inhibitors for synthetic rubbers lubricating oils etc. The aromatic ring is usually unsubstituted but may be substituted by one or more alkyl groups, for instance containing 5 to 15 carbon atoms. The amides may be added in the form of the phenolate salts with alkali metals or alkaline earth metals.

A new compound according to the present invention is a multivalent metal ion salt of a compound of the formula $XNR^1R^2$, in which $R^1$ and $R^2$ are the same or different and each are selected from hydrogen and hydrocarbon based radicals having from 1 to 30 carbon atoms, X is an acyl radical of an aromatic ortho-hydroxy carboxylic acid having a ring substituent which is a hydrocarbon based radical having at least 4 carbon atoms. The salt is oil-soluble.

Usually the multivalent metal ion is a divalent metal ion and is preferably an alkaline earth metal ion, for instance selected from Sr, Ba, Mg or Ca, usually Mg, preferably Ca.

Preferably at least one of $R^1$ and $R^2$ is a group other than hydrogen. Preferably one of $R^1$ and $R^2$ is hydrogen. A hydrocarbon based radical represented by $R^1$ and/or $R^2$ is attached via a carbon atom to the amide nitrogen atom and may be aliphatic, alicylic, aromatic, alkaryl, aralkyl. In one class of preferred compounds the alkyl radical is a lower alkyl radical, for instance having 1 to 6 carbon atoms. Another class of compounds has a long chain alkyl group for instance having 4 to 24 carbon atoms. Any alkyl chains may be branched or straight chain. It may for instance be a radical in which the carbon atom attached to the nitrogen atom is a secondary or tertiary carbon atom. The radical may contain non-hydrocarbon substituents which do not alter the predominantly hydrocarbon character of the radical such as halogen atoms, nitro groups, cyano groups, ether groups, ester groups, amide groups, ketone groups, sulphone groups and sulphoxide groups, as well as chains with hetero atoms, such as oxygen, sulphur, or nitrogen atoms.

The aromatic radical may comprise a napthalene ring or, preferably, a benzene ring. Where the ring is a naphthalene ring, the compound may have the hydroxyl and carbonyl groups attached to the ring at any available positions, as long as they are ortho to each other. The aromatic ring may comprise substituents other than the hydrocarbon substituent, which do not interfere the activity of the compound as an oxidation inhibitor or with the process for producing the compound. For instance it may comprise other hydrocarbon substituents, such as lower alkyl substituents, as well as halogen atoms, sulpho groups and amino groups. Usually there are no additional substituents.

The hydrocarbon-based ring substituent is a radical having a carbon atom directly attached to the ring and has a predominantly hydrocarbon character, i.e., promotes oil solubility. It is usually in the position ortho or gas to the hydroxyl group but meta is also possible. Examples of of such radicals are hydrocarbon radical such as aliphatic, alicyclic, aromatic, alkaryl or aralkyl usually a C8 to 30, preferably C10 to 24-alkyl group, which may branched or straight chain; substituted hydrocarbon radicals, i.e. radicals containing non-hydrocarbon substituents which do not alter the predominantly hydrocarbon, hydrophobic character of the radical, such as halogen atoms, nitro groups, cyano groups, ether groups, ester groups, amide groups, ketone groups, sulphone groups and sulphoxide groups, as well as chains with hetero atoms, such as oxygen, sulphur, or nitrogen atoms.

It is most convenient for the group X to comprise the acyl radical of a $C_6$ to 30 alkyl salicyclic acid.

The product of the invention is preferably "overbased", that is it comprises a greater than stoichiometric amount of metal than required to neutralise the phenolate ion. Overbased products can be described in terms of their "basicity index" (BI), which is defined as the ratio of total equivalents metal to equivalents of the acyl groups (or amide groups) in the X group of the compound. An overbased product generally has excess of metal (hydr)oxide and may also comprise the carbonate of the metal. An amide overbased with lime and which is subsequently carbonated may for instance be represented by the following formula:

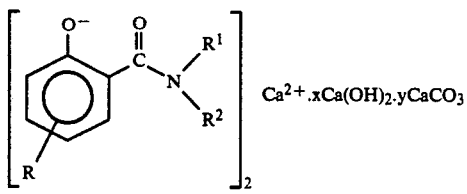

There is also provided in the invention a process for producing the new compounds, in which a compound of the formula XY is reacted with an amine of the formula $HNR^1R^2$, in which Y is $OR^3$, in which $R^3$ is hydrogen, alkyl, aryl or acyl, or Y is a halogen atom, and $R^1$ and $R^2$ are as defined above, followed by the reaction of the amide with a multivalent metal compound to produce the salt.

Usually the metal compound with which the amide is reacted includes the metal oxide or hydroxide. Preferably the metal compound is added in greater than stoichiometric, or equivalent, amounts, to give an overbased product. Usually the reaction to produce the salt is followed by a carbonation reaction for instance carried out as described in Great Britain Patent No. 8613815, Great Britain Patent No. 8627130 or Great Britain Patent No. 871159.

The amidation of the present invention uses the ring-substituted acid or derivative as its starting material. In general these are readily available and it has been found that it is easier to carry out that amidation than a process in which the amide of an unsubstituted aromatic acid is subsequently reacted to introduce the required substituent into the ring.

Although the process may be carried out using the acid as the starting material, it is generally found to be preferred for the process to use a derivative of the acid as its starting material, for instance the acid chloride or acid anhydride or most conveniently the ester. Usually the ester is formed from the acid by reaction with a C1 to 6 alkanol by conventional esterification techniques. It is convenient for the alcohol to have at least 3 atoms, for instance 4 atoms, since the esterification reaction can then be driven by removal of water and a higher reaction temperature can be used.

The amidation process starting from the ester is usually carried out with an excess of the amine. Excess amine and the alcohol which is produced are removed from the product by distillation.

In the amidation reaction using the acid chloride as the starting material it is important to remove the hydrogen chloride which is formed as a by-product. In general this is done by washing with water, in the normal way. This route is less preferred than starting with the ester because of the difficulty of ensuring complete removal of chloride or other halide.

In an alternative process for producing the new products, the acid X-OH may be reacted with urea, or a thiourea or substituted ureas. Reaction with urea produces the amide which can, if desired, be subsequently alkylated by known techniques.

The reaction to produce the salt is carried out by conventional techniques, for instance by reaction with a metal compound, usually a (hydr)oxide, in organic solution, for instance in a solvent comprising xylene and methanol. As stated above the product is preferably an overbased product, that is formed by a reaction in which there is a stoichiometric excess of metal compound added. Such an overbasing reaction may for instance be carried out as described in Great Britain A-786167. Usually the overbasing reaction additionally comprises a carbonation step, in which the product of the reaction between an excess of metal compound and amide in a solvent solution is contacted with carbon dioxide at a slightly raised temperature. Such processes are for instance as described in Great Britain Patent No. 8613815, Great Britain Patent No. 8627130 and Great Britain Patent No. 8716159.

The product may optionally be borated as described in Great Britain Patent No. 8330441.

The invention provides also for the use of new compounds as additives in lubricating oils, greases or other oil-based systems. For instance, the compounds have oxidation inhibiting properties and may be used in any of the applications where an oil-soluble oxidation inhibitor is required, for instance in polymer composition, including rubbers, and in various viscous organic liquids, such as oils and greases. The compounds also have detergent and dispersant properties in lubricating systems and their use in those compositions can additionally give improved friction properties as well as oxidation stability.

The compounds of the present invention are found to have properties which are similar to the overbased salicyclic acid compounds described in the above mentioned publication. The compounds are thought to form micelles in oil solution, in which the inorganic base particles ($Ca(OH)_2$, $CaCO_3$, MgO, etc) can be incorporated to generate a colloidal, for instance overbased, but oil-soluble detergent. The alkaline reserve of the overbased products allows neutralisation of acidic compounds formed during the operation of an engine which is lubricated by a composition containing the compounds.

Lubricating oil compositions in the invention comprise a major amount of a lubricating base oil and minor amount of the salt as described hereinbefore.

The lubricating base oil will conveniently constitute more than 50% w, preferably more than 80% w, of the composition. It can be selected from mineral lubricating oils of varying viscosities, but it also includes a synthetic lubricant, such as ester-type lubricant or a polyolefin-type fluid, or a vegetable oil, or a grease.

Fuel compositions which are used in marine diesel engines usually contain some sulphur compounds. To neutralize the acidic compounds formed from these sulphur compounds a relatively high concentration of the basic salt is employed. Preferably, these marine lubricating oil compositions contain from 5 to 30% w of the salt. Lubricating oil compositions for road engines may contain lower concentrations. The amount of salt in these lubricating oil compositions is preferably from 0.01 to 5% w, in particular from 0.1 to 4.0% w.

Fuels, such as gasolines, kerosine, diesel fuel and gas oils, can also contain the above salts. The amount of these salts is similar to that in road engine lubricating oil compositions or lower; conveniently the amount is from 0.001 to 5% w, in particular from 0.01 to 1.0% w.

The lubricating oil composition can be prepared by mixing a concentrate containing a major portion of salt, i.e., containing up to 60% w of a salt as described above, in a lubricating oil, with a lubricating base oil to give the desired concentration. The composition should contain a major portion of base oil, i.e., greater than 50% w, and a minor portion of salt, i.e., less than 50% w. Such a concentrate is conveniently prepared by addition of a lubricating oil to the product obtained after completion of step c), and removal of any volatile hydrocarbon solvent, water and alcohol, if present. The lubricating oil may be the same as the one indicated above as a suitable hydrocarbon solvent. The concentrate may conveniently contain a stabiliser, which is selected from a variety of organic compounds, such as those described in British patent specification No. 818,315. These compounds include mono- or polyhydric alcohols, alkyl amines and alkyl phenols.

The lubricating oil compositions may further contain a number of other additives, such as antioxidants, foam inhibitors, corrosion inhibitors, viscosity index improvers, and pour point depressants, as can be established by a person skilled in the art. The compounds can be used in combination with other dispersants and detergents.

The ranges and limitations provided in the instant specification and claims are those which are believed to particularly point out and distinctly claim the instant invention. It is, however, understood that other ranges and limitations that perform substantially the same function in substantially the same way to obtain substantially the same result are intended to be within the scope of the instant invention as defined by the instant specification and claims.

EXAMPLES

The invention will be described by the following examples which are provided for illustrative purposes and are not to be construed as limiting the invention:

EXAMPLE 1 a) The preparation of C14–18 alkylsalicylic-n-butyl-ester

At room temperature 8 ml of $H_2SO_4$ was added to a mixture of 103.6 g (0.2 mol) of solvent-free $C_{14-18}$ alkylsalicylic acids (1.93 meq/g) and 148 g (2 mol) of n-butanol. After a slight rise in temperature the reaction mixture was further heated to reflux temperature (about 118° C.) for 5 hours. The mixture was cooled down, 250 ml of water was added, stirred and phase separated. The organic layer was washed with a concentrated sodium bicarbonate solution until all the free acid was removed, and with water. The product was dried over anhydrous magnesium sulphase and the solvents were removed in a rotary evaporator at 100° C., 4 mm Hg (533 Pa) for 2 hours to yield the ester. Its identity was confirmed by infrared spectroscopy which had a characteristic C=O peak at 1675 $cm^{-1}$.

b) The preparation of C14–18 alkylsalicylic-n-butyl-amide

After the addition at room temperature of 17 g (0.23 mol) of n-butylamine to 83.6 g (0.15 mol) of the ester produced in a) the temperature was increased to reflux (about 115° C.). After 6 hours of reflux, the formed n-butanol and the remainder of the n-butylamine were distilled off and another 17 g of n-butylamine was added. In total three sequences as described above were carried out to obtain complete conversion of the ester to the desired amide (monitored by IR). The n-butyl-amide was finished in the rotary evaporator at 100° C. 4 mm Hg (533 Pa) for 2 hours. It's identity was confirmed by infrared spectroscopy which had a characteristic amide C=O peak at 1645 cm−1. Also analysis showed the N content as 2.61% by weight (theoretical 2.46% weight).

EXAMPLE 2 a) The preparation of C14–18 alkylsalicyclic acid chloride

Under nitrogen blanket 242.5 g (2.04 mol) of thionychloride was added to 700 g (1.36 mol) of solvent-free $C_{14-18}$ alkylsalicylic acids (1.93 meq/g) during 1 hour at 22° C. In the next three hours the temperature was slowly raised to 150° C. The formed HCl and $SO_2$ were trapped in a caustic scrubber. The product was cooled and two times 200 ml of benzene was added and distilled off. The finished AC-acid chloride was stored under nitrogen.

b) The preparation of C14–18 alkylsalicylic n-butyl-amide

In two hours 29.2 g (0.4 mol) of n-butylamine was added to 107 g (0.2 mol) of the acid chloride produced in a) while the temperature of the reaction mixture was kept below 28° C. with the aid of an ice bath. The temperature was then slowly increased to 42° C. and kept at that temperature for 1.5 hours. The reaction mixture was washed with 200 ml of water twice, dried over magnesium chloride and filtered over "Hyflo" filter aid. The n-butyl-amide was finished in the rotary evaporator at 100° C., 4 mm Hg (533 Pa) for 2 hours. The infrared spectrum had a characteristic amide C=O peak. Analysis showed the N content to be 2.68% weight.

EXAMPLE 3

Neutralization and Overbasing

The amides produced in Examples 1 and 2 were reacted with lime in a (xylene and amide) methanol, 90/10 solution such that four equivalents of lime were added per equivalent of amide. The neutralisation reaction was carried out at 53° C. for 1 hour. Then the solution was dosed with carbon dioxide at a rate of 1 ml carbon dioxide per meq amide per minute at 55° C. until a total of 1.6 equivalents carbon dioxide per equivalent of amide had been added. Reaction mixture was centrifuged for two hours at 2500 ppm to separate out the solids. The methanol layer was then removed and to the solution of overbased amide in xylene was added a proportion of base oil and xylene was removed in a rotary evaporator at 4 mm Hg (533 Pa) at 100° C. for 2 hours. The amount of base oil was dependent on the desired Ca concentration. This produced overbased products in oil in which the product via the ester route of Example 1 above had a basicity index defined as equivalent Ca/equivalent N or amide of 2.3, and in which the product formed via the acid chloride route described in Example 2 above has a basicity index of 1.7.

EXAMPLE 4

The products of Example 3 were then tested in a range of performance tests, and were compared with known compounds, including the corresponding acid in its unneutralised form as well as an overbased form with a BI of 3.0 defined as equivalents Ca/equivalents acid, the ester intermediate formed in Example 1a) the unneutralised amide as well as unneutralised amides formed from polyamines similar to those described in US-A-

4090971. The tests that were carried out were as follows:

Non-engine performance (NEP) tests

Differential Scanning Calorimetry (DSC)

DSC is used as a tool to study the antioxidant performance of an additive. The oil being tested is heated at a controlled rate until exothermic reaction is detected. The temperature at which the oxidation is initiated is the DSC onset temperature. A higher temperature indicates an improved oxidation resistance of the oil. The results of the DSC evaluations are compiled in Table 1. The tests use a rate of temperature increase of 16° C. per minute and the results reported are averages of between and 2 and 4 determinations.

TABLE 1

| Additive | DSC Onset Temp. °K. |
|---|---|
|  | 470 |
| overbased n-butyl amid (via Ex. 1) | 476 |
| n-butyl amide | 482 |
| acid | 484 |
| overbased acid | 481 |
| n-butyl ester | 477 |
| TETA amide | 474 |
| ED amide | 476 |
| BD amide | 481 |

TETA amide ED amide and BD amide are, respectively, the amides produced by replacing n-butylamine in Example 1b) by triethyltetramine, ethylene diamine and butylene diamine.

In general, it seems that any modification of the AC-acids (conversion to ester, amide or an overbased product) results in a slightly lower DSC onset temperature, however, the observed differences are not considered to be significant. The overbased n-butyl amide does show a directional improvement in oxidation stability relative to the undoped reference oil.

Carbon Black Dispersancy Test

Dispersancy in this test is evaluated by measuring the change in the viscosity of a lubricating oil based on a Brent base oil mixture at 60° C. that occurs by the addition of 3% m carbon black. Tests were carried out comparing the overbased n-butylamide with the overbased acid (BI 2.4) both products based on the same batch of acids and also with a commercially available overbased calcium alkylsalicylate additive containing 40% w mineral oil and having density at 20° C. of 0.993 kg/1, viscosity at 40° C. (ASTM D445) of 170 mm²s, calcium content of 6.0% w, and total base number of 165 mg KOH/g"). All products were compared at equivalent calcium contents. Results (Table 2) show no difference in % viscosity increase between the detergents used, indicating that the overbased amide is as effective as the overbased acid in soot dispersancy in this particular rig test.

TABLE 2

| Additive | Viscosity at 60° C. (initial) mm²-/s | Viscosity at 60° C. (final) mm²/s | Viscosity increase % |
|---|---|---|---|
| Overbased acid (same acid starting materials) | 28.40 | 44.00 | 55.1 |
|  | 28.40 | 47.20 | 63.3 |
| Overbased amide of Ex 1 | 27.89 | 44.46 | 59.4 |
|  | 27.89 | 42.81 | 53.5 |
| Commercial Product | 39.50 | 60.52 | 53.2 |
|  | 39.50 | 61.89 | 56.7 |

Boundary Lubrication Friction Characteristics

This test uses a modified 4-bore test as described by Morecroft in "Wear" 89 215 (1983). The friction characteristics of the overbased amide used in the preceding tests and the commercially available overbased acid used in the preceding test were determined by incorporating those compounds at an equal soap content in a simple formulation based on Brent base oil containing 0.5% m zinc dithophosphate.

The results, shown in Table 3, show that there is a large reduction in friction coefficient using the overbased amide compared to the reference oil containing no additive, although there is a small deficit in the friction reduction compared to the commercially available overbased acid.

TABLE 3

| Additive | Mean friction | Reduction relative to base formulation (%) |
|---|---|---|
| — | 0.1265 | — |
| 6% overbased acid | 0.0836 | 33.9 |
| 16.7% overbased amide | 0.0901 | 28.8 |

Cam and Tappet tribometer test

Friction reduction properties of a range of experimental products were also studies by using the cam an tappet tribometer as described in detail in SAE paper 850441 by van Helden et al. Using a base oil to which an increasing amount of friction modifier is added, this test measures the change of the friction in a cam/tappet contact relative to the base oil. The rig was operated at 100° C. and a rotation speed of 800 rpm. The base oil was Vitrea 100 ($V_k100=11$ mm²/s), to which 1% m of a zinc dithiophosphate EP/AW additive was added. This additive is normally added to reduce wear at the cam/toppet contact. It was ensured that the results of this study were not influenced by the presence of that additive. Tests were carried out using the overbased amide as well as the other compounds listed in Table 1 above. The results are reported in Table 4.

TABLE 4

| Entry | Product Type | Additive Concentration (% m) | % Friction Reduction # (max) |
|---|---|---|---|
| 1 | acid | 1.6* | 19 |
| 2 | overbased acid | 2.0 | 6 |
| 3 | n-butylamide | 0.9 | 12 |
| 4 | overbased n-butylamide | 0.7 | 8 |
| 5 | ED amide | 1.7* | 21 |
| 6 | HD amide | 0.1 | 16 |
| 7 | n-butyl ester | 1.8 | 10 |
| 8 | TETA amide | 0.5 | −34 |

HD is hexylenediamine
relative to base oil (Vitrea 100)
*highest concentration measured in this series Engine Performance Evaluations Sequence 5D engine test An area in which detergents and dispersants have an important influence on engine performance is engine cleanliness (e.g. varnish and sludge formation) and wear, which is evaluated for gasoline engines in the ASTM Sequence 5D test. In this test engine cleanliness and valve train wear are assessed in a cyclic operating procedure designed to simulate driving conditions under low temperature stop-go operating conditions. Generally the degree of valve train were protection given by an oil is governed by the choice and amount of extreme pressure additive, usually a zinc dithiophosphate (ZDTP). The degree of valve train wear also responds to variations in metal containing detergent and ashless dispersant components in a formulated oil. Therefore, the Sequence 5D test is an important tool in the evaluation of new detergent types; possible wear and cleanliness benefits and/or deficits can conveniently be identified.

The overbased amide was compared with the commercially available overbased acid used in the carbon black dispersancy test above on equivalent calcium content using a 0.87 % wt sulphated ash, SAE 30 grade formulation. Duplicate tests were carried out on both oils and the test results are shown in Table 5. In the tests, the overbased amide showed no improvement in sludge or varnish control relative to the overbased acid containing oil. The average (and maximum) cam lobe wear data show a directional improvement in performance by substituting overbased amide for overbased acid; the differences are, however, not statistically significant. The cleanliness data indicate that the overbased salicylamide has no improved detergent/dispersant character. It is possible that a deficit in detergent performance, originating from the introduction of nitrogen is compensated by improved dispersancy.

TABLE 5

| Additive | Amount % m | *Av. sludge | *Av. varnish | *Piston Av. skirt varnish | Av. Cam lobe wear ($10^{-3}$ in) | Max cam lobe wear ($10^{-3}$ in) |
| --- | --- | --- | --- | --- | --- | --- |
| Overbased amide | 3.55 | 9.51 | 6.57 | 7.26 | 0.39 | 0.60 |
|  |  | 9.53 | 6.96 | 7.54 | 0.39 | 0.70 |
| Overbased acid | 2.00 | 9.50 | 6.33 | 7.56 | 0.49 | 0.60 |
|  |  | 9.58 | 7.28 | 7.52 | 0.70 | 1.10 |
| +API SF Pass Limits |  | >9.4 | >6.6 | >6.7 | 1.0 | 2.5 |

*10 = clean + For comparison

What is claimed is:

1. An oil soluble trivalent, or higher valence, metal ion salt of a compound of the formula $XNR^1R^2$, in which $R^1$ and $R^2$ are the same or different and each are selected from hydrocarbon based radicals having from 1 to 30 carbon atoms, X is an acyl radical of an aromatic ortho-hydroxy carboxylic acid having a ring substituent which is a hydrocarbon based radical having at least 4 carbon atoms.

2. A process for producing an amide as defined in claim 1 in which a compound of the formula XY is reacted with an amine of the formula $HNR^1R^2$, in which X is in acyl radical of an aromatic ortho-hydroxy carboxylic acid having a ring substituent which is a hydrocarbon based radical having at least 4 carbon atoms and Y is $OR^3$ in which $R^3$ is a $C_{1-6}$-alkyl group, followed by the reaction of the amide with a trivalent metal compound which comprises the oxide or hydroxide of the metal and wherein the metal compound is added in greater than stoichiometric amounts for neutralizing the phenolate moiety to give an overbased product and wherein the process includes a carbonation step.

* * * * *